(12) United States Patent
Decook et al.

(10) Patent No.: US 11,378,491 B2
(45) Date of Patent: Jul. 5, 2022

(54) BEARING FRAME MONITORING SYSTEM

(71) Applicant: ITT Manufacturing Enterprises LLC, Wilmington, DE (US)

(72) Inventors: Brad Decook, Victor, NY (US); Daniel Kernan, Syracuse, NY (US); James Reitano, Farmington, NY (US)

(73) Assignee: ITT Manufacturing Enterprises LLC, Wilmington, DE (US)

( * ) Notice: Subject to any disclaimer, the term of this patent is extended or adjusted under 35 U.S.C. 154(b) by 174 days.

(21) Appl. No.: 16/839,757

(22) Filed: Apr. 3, 2020

(65) Prior Publication Data
US 2021/0310901 A1    Oct. 7, 2021

(51) Int. Cl.
*G01M 13/045*    (2019.01)
*G01N 33/28*    (2006.01)
(Continued)

(52) U.S. Cl.
CPC ......... *G01M 13/045* (2013.01); *G01F 23/263* (2013.01); *G01F 23/292* (2013.01);
(Continued)

(58) Field of Classification Search
CPC .... G01F 23/263; G01F 23/292; G01F 23/296; G01K 13/00; G01M 13/045; G01N 33/2888; G01P 3/44
See application file for complete search history.

(56) References Cited

U.S. PATENT DOCUMENTS 2,420,177 A * 5/1947 Krall .................... F16N 29/04
200/61.09
3,869,391 A * 3/1975 Kramer ................ F15B 21/041
210/222
(Continued)

FOREIGN PATENT DOCUMENTS

AU    2017269731 A1 * 11/2018 ............ F16C 19/527
CN    104297003 A * 1/2015
(Continued)

OTHER PUBLICATIONS

Make Any Motor A Smart Motor, ITT, Inc., available on the internet at Dec. 10, 2018 and Jan. 6, 2019. (Year: 2019).*
(Continued)

*Primary Examiner* — David A. Rogers
(74) *Attorney, Agent, or Firm* — Mannava & Kang P.C.

(57) ABSTRACT

Technologies are generally described for an integrated monitoring system to monitor several operational aspects of a bearing assembly, analyze monitored aspects, provide predictions, alerts, and reports based on general equipment data or specific rotating machine data. A number of sensors in and on a bearing housing may sense a variety of operational aspects and provide input to a local or remote monitoring device. The bearing housing may include sensor mounting locations for one or more sensors. In some examples, an oil level sensor placed in a suitable mounting location on the bearing housing may detect oil levels inside the bearing housing. The monitoring device may analyze the sensor
(Continued)

inputs in light of other information such as historic performance data, environmental information, etc. Reports, predictions, alerts, and/or suggested corrective actions may be generated based on the analysis by the monitoring device and/or remote devices communicatively coupled to the monitoring device.

20 Claims, 6 Drawing Sheets

(51) Int. Cl.
    *G01P 3/44*           (2006.01)
    *G01F 23/296*      (2022.01)
    *G01F 23/263*      (2022.01)
    *G01F 23/292*      (2006.01)
    *G01K 13/00*       (2021.01)

(52) U.S. Cl.
    CPC ........... *G01F 23/296* (2013.01); *G01K 13/00* (2013.01); *G01N 33/2888* (2013.01); *G01P 3/44* (2013.01)

(56) References Cited

U.S. PATENT DOCUMENTS

| | | | | |
|---|---|---|---|---|
| 4,030,028 A * | 6/1977 | Allender | ............... | F01M 11/10 324/698 |
| 4,237,454 A | 12/1980 | Meyer | | |
| 4,304,132 A * | 12/1981 | Snaper | ................. | F02D 33/003 340/620 |
| 4,410,885 A * | 10/1983 | Stenstrom | .............. | F01M 11/10 123/196 S |
| 4,741,204 A * | 5/1988 | Luck | ................. | G01N 33/2876 436/61 |
| 5,089,780 A * | 2/1992 | Megerle | ............ | G01N 33/2888 324/444 |
| 5,381,692 A | 1/1995 | Winslow et al. | | |
| 5,911,289 A * | 6/1999 | Waller | ................. | F25B 31/002 184/103.2 |
| 5,956,995 A * | 9/1999 | Herben | ................... | G01F 23/30 73/314 |
| 5,960,772 A * | 10/1999 | Tracy | ..................... | G01L 23/222 123/406.4 |
| 6,035,702 A * | 3/2000 | Graham | ................. | B63B 13/00 73/49.8 |
| 6,078,874 A * | 6/2000 | Piety | ..................... | G01H 1/003 702/122 |
| 6,206,108 B1 * | 3/2001 | MacDonald | ......... | E21B 49/005 175/24 |
| 6,208,944 B1 * | 3/2001 | Franke | ................. | G01H 1/003 340/680 |
| 6,276,901 B1 * | 8/2001 | Farr | .................... | F04B 39/0207 340/619 |
| 6,513,386 B2 * | 2/2003 | Barclay | ............... | G01M 13/028 73/649 |
| 6,546,814 B1 * | 4/2003 | Choe | ..................... | G01H 1/003 73/862.08 |
| 6,913,438 B2 * | 7/2005 | Rockwood | .............. | F01D 25/18 184/104.1 |
| 6,964,518 B1 * | 11/2005 | Jagtøyen | .................. | F16C 9/04 374/154 |
| 7,097,351 B2 | 8/2006 | Lancon et al. | | |
| 7,134,323 B1 * | 11/2006 | Discenzo | ........... | G01N 33/2888 73/53.05 |
| 7,328,081 B2 * | 2/2008 | Kluft | .................. | G05B 19/4065 700/175 |
| D583,396 S * | 12/2008 | Playford | ...................... | D15/143 |
| D583,841 S * | 12/2008 | Playford | ...................... | D15/143 |
| 7,493,799 B1 * | 2/2009 | Discenzo | ................ | F16C 19/52 184/108 |
| 7,624,618 B2 * | 12/2009 | Bader | ................. | F01M 11/0408 116/104 |
| 7,690,246 B1 * | 4/2010 | Discenzo | ............... | G01N 33/30 73/53.05 |
| 7,788,973 B2 * | 9/2010 | Quill | ....................... | F04B 53/16 73/323 |
| 8,156,787 B2 * | 4/2012 | Asanuma | ............. | G01N 33/287 73/23.33 |
| 8,342,013 B2 * | 1/2013 | Nedachi | ............. | G01N 33/2888 73/114.55 |
| 8,464,576 B2 * | 6/2013 | Okuyama | ................ | F01M 1/18 73/53.01 |
| 8,590,384 B2 * | 11/2013 | Lotscher | ................ | G01H 11/08 73/661 |
| D729,291 S * | 5/2015 | Hawa | .......................... | D15/123 |
| D729,292 S * | 5/2015 | Hawa | .......................... | D15/123 |
| 9,260,989 B2 * | 2/2016 | Kock | ..................... | F01M 11/12 |
| 9,354,125 B2 * | 5/2016 | Peroulis | .................. | G01P 15/11 |
| 9,759,636 B2 * | 9/2017 | Murphy | .................. | H04W 4/70 |
| 9,805,525 B2 * | 10/2017 | Slama | ................. | G06F 11/0745 |
| D807,924 S * | 1/2018 | Wilkie | ............... | D15/7 |
| D832,900 S * | 11/2018 | Tuttle | ............... | D15/143 |
| 10,125,768 B2 * | 11/2018 | Brostrom | ............ | F04B 39/0284 |
| 10,180,139 B2 * | 1/2019 | Brostrom | ............ | F04C 18/16 |
| 10,634,112 B2 * | 4/2020 | Hofmann | .............. | F03B 11/006 |
| 10,648,509 B2 * | 5/2020 | Bradshaw | ............. | F16C 19/522 |
| 10,705,039 B2 * | 7/2020 | Kiriyama | ............. | G01N 33/2858 |
| 10,705,517 B1 * | 7/2020 | Dresang | ................. | H04W 4/38 |
| 10,718,200 B2 * | 7/2020 | Coste | .................... | E21B 47/008 |
| 10,748,406 B2 * | 8/2020 | Boerhout | ................ | G06F 1/163 |
| 10,947,968 B2 * | 3/2021 | Decook | ................... | F04B 51/00 |
| 10,969,303 B2 * | 4/2021 | Sepe | ...................... | F16C 19/527 |
| 10,969,375 B1 * | 4/2021 | Bayyouk | ........... | G01N 33/2888 |
| 10,976,379 B2 * | 4/2021 | Williams | ........... | G01R 33/0017 |
| 11,085,489 B2 * | 8/2021 | Epps | ..................... | G01M 13/045 |
| 2006/0178771 A1 * | 8/2006 | Kluft | .................. | G05B 19/4065 700/177 |
| 2011/0137587 A1 * | 6/2011 | Rothlisberger | ........ | B65G 43/00 702/56 |
| 2016/0290191 A1 * | 10/2016 | Staley | ................. | F01M 11/0408 |
| 2020/0256746 A1 * | 8/2020 | Lowry | ................... | G01K 13/08 |

FOREIGN PATENT DOCUMENTS

| | | | | |
|---|---|---|---|---|
| CN | 109524139 A | * | 3/2019 | ............ G01F 23/00 |
| EP | 1425640 B1 | * | 11/2006 | ......... G05B 19/4065 |
| WO | 1994013968 A3 | | 10/1994 | |

OTHER PUBLICATIONS

ESPACENET Machine Translation of CN 109524139 A Which Originally Published on Mar. 26, 2019. (Year: 2019).*

* cited by examiner

BEARING FRAME MONITORING SYSTEM

BACKGROUND

Unless otherwise indicated herein, the materials described in this section are not prior art to the claims in this application and are not admitted as prior art by inclusion in this section.

A centrifugal pump is rotating machine designed to move a fluid by transferring rotational energy through driven rotors to impellers. Fluid enters the centrifugal pump at an intake port, where the impeller is located. A driver is utilized to rotate a shaft that is connected to the impeller, thereby controlling the rotation of the impeller. The rotational motion of the impeller generates a centrifugal force that increases the velocity of the fluid so that the fluid flows through the pump casing to an outlet. Centrifugal pumps, as well as other rotating machines, include bearings to provide stability, mechanical efficiency, and structural configuration.

Bearing assemblies in centrifugal pumps and other rotational machines may be configured to include sealed lubrication to protect moving components. Yet, as any machine with moving components, bearing assemblies are subject to failure over their lifetime. Failure of the bearing assembly may result in termination of operation for the pump or worse, catastrophic failure of the centrifugal pump.

SUMMARY

The present disclosure generally describes an integrated monitoring system to monitor several operational aspects of a bearing assembly, analyze monitored aspects, provide predictions, alerts, and reports based on general equipment data or specific pump data.

According to some examples, a monitoring system for a rotating machine is described. The monitoring system may include a first sensor and a second sensor mounted in a bearing housing of the rotating machine, where the first sensor is an oil level sensor mounted at a location in the bearing housing suitable to detect a lubricant oil level inside the bearing housing and the second sensor distinct is from the first sensor; and a monitoring device communicatively coupled to the first sensor and second sensor. The monitoring device may include a communication sub-system to facilitate communication with the first sensor and second sensor; a memory configured to store instructions; and a processor coupled to the communication sub-system and the memory. The processor, in conjunction with the instructions stored in the memory, may receive sensor inputs from the first sensor and second sensor; perform an analysis of the received sensor inputs, where the analysis includes application of a dynamic threshold in evaluation of each sensor input based on one or more other sensor inputs; and generate an alert based on a result of the analysis.

According to other examples, the communication sub-system may be further configured to facilitate one or more of wired and wireless communication with one or more remote devices. The processor may be further configured to transmit the generated alert to the one or more remote devices, where the alert includes one or more of a prediction, a report, or a suggested corrective action; and transmit raw or processed sensor inputs to the one or more remote devices such that at least a portion of the analysis is performed by the one or more remote devices, where the one or more remote devices include a distributed control system (DCS), a server, a stationary computing device, a portable computing device, a special purpose computing device, or an output device.

According to further examples, the processor may be further configured to receive one or more of historical data or environmental data, where the historical data includes one or more of generic rotating machine specifications, specific rotating machine specifications, historic performance data for the rotating machine, or historic failure data for the rotating machine, and the environmental data includes one or more of ambient temperature, ambient vibration levels, fluid pressure, fluid temperature, fluid viscosity, or a supply power condition; and perform the analysis of the received sensor inputs in conjunction with the received one or more of historical data or environmental data.

According to yet other examples, the processor may be further configured to transmit one or more of reset or configuration instructions to the first sensor and second sensor. The second sensor may include an oil temperature sensor configured to measure a temperature of the lubricant oil, a bearing housing temperature sensor configured to measure a temperature of the bearing housing, a vibration sensor configured to collect vibration data in at least two orthogonal directions, a relative humidity sensor configured to sense one or more of a presence of water or a concentration of water in a lubricant of the bearing housing, an oil contamination sensor configured to sense one or more of a presence of a contaminant or a concentration of the contaminant in the lubricant oil, a magnetic sensor configured to sense a rotational speed of a shaft of the rotating machine, a pressure sensor configured to measure a pressure of the lubricant oil, or a flow sensor configured to measure a flow rate of the lubricant oil through a filtering system.

According to some examples, each of the first sensor and second sensor may be mounted inside or on the surface of the bearing housing permanently or removably, and a location of each sensor may be selected based on one or more of a sensor type, a bearing housing type, or a bearing housing configuration. The location in the bearing housing suitable to mount the oil level sensor may be selected based on one or more of a size of a bearing, a configuration of the bearing, an inside volume of the bearing housing, or a type of the lubricant oil. The first sensor and second sensor may be configured to collect sensor data periodically, on-demand, or continuously.

According to other examples, a monitoring system for a rotating machine is described. The monitoring system may include a first sensor and a second sensor mounted in a bearing housing of the rotating machine, where the first sensor is an oil level sensor mounted at a location in the bearing housing suitable to detect a lubricant oil level inside the bearing housing and the second sensor distinct is from the first sensor; a remote computing device; and a monitoring device communicatively coupled to the first sensor and second sensor and the remote computing device. The monitoring device may include a communication sub-system to facilitate communication with the first sensor and second sensor and the remote computing device; a memory configured to store instructions; and a processor coupled to the communication sub-system and the memory. The processor, in conjunction with the instructions stored in the memory, may receive sensor inputs from the first sensor and second sensor; transmit at least a first portion of the received sensor inputs to the remote computing device; perform an analysis on a second portion of the received sensor inputs, where the analysis includes application of a dynamic threshold in evaluation of each sensor input of the second portion based on one or more other sensor inputs; and generate an alert based on a result of the analysis.

According to further examples, the remote computing device may be configured to receive one or more of historical data or environmental data, where the historical data includes one or more of generic rotating machine specifications, specific rotating machine specifications, historic performance data for the rotating machine, or historic failure data for the rotating machine, and the environmental data includes one or more of ambient temperature, ambient vibration levels, fluid pressure, fluid temperature, fluid viscosity, or a supply power condition; perform an analysis on the first portion of the received sensor inputs in conjunction with the received one or more of historical data or environmental data, where the analysis includes application of a dynamic threshold in evaluation of each sensor input of the first portion based on one or more other sensor inputs; and generate a report based on a result of the analysis. One or more of the historical data and the environmental data may be stored at least partially in one or more of the monitoring device, the remote computing device, or a database communicatively coupled to the remote computing device.

According to yet other examples, the monitoring device may be mounted on the bearing housing or integrated with the remote computing device. The oil level monitoring device may include capacitive interdigitated electrodes, an optical sensor, an ultrasound sensor, or an electromechanical sensor. The first sensor may include an oil temperature sensor, a bearing housing temperature sensor, a vibration sensor, a relative humidity sensor, an oil contamination sensor, a pressure sensor, a flow sensor, or a magnetic sensor. The processor may be configured to employ one or more of a machine learning algorithm or an artificial intelligence algorithm to perform the analysis and to generate one or more of a prediction, the alert, a report, or a suggested corrective action.

According to some examples, a method to monitor operational health of a rotating machine assembly is described. The method may include receiving sensor inputs from a first sensor and a second sensor mounted in a bearing housing of the rotating machine assembly, where the first sensor is an oil level sensor mounted at a location in the bearing housing suitable to detect a lubricant oil level inside the bearing housing and the second sensor distinct is from the first sensor; transmitting at least a first portion of the received sensor inputs to a remote computing device; receiving external data associated with the rotating machine assembly; performing an analysis on a second portion of the received sensor inputs in conjunction with the received external data by applying a dynamic threshold in evaluation of each sensor input of the second portion based on one or more other sensor inputs; and generating an alert that includes a suggested corrective action based on a result of the analysis.

According to other examples, transmitting at least the first portion of the received sensor inputs to the remote computing device may include facilitating performance of an analysis, by the remote computing device, on the first portion of the received sensor inputs in conjunction with the received external data by applying a dynamic threshold in evaluation of each sensor input of the first portion based on one or more other sensor inputs; and facilitating generation of another alert, by the remote computing device, based on a result of the analysis. Receiving the external data may include receiving one or more of generic rotating machine specifications, specific rotating machine specifications, historic performance data for the rotating machine, or historic failure data for the rotating machine, and one or more of ambient temperature, ambient vibration levels, fluid pressure, fluid temperature, fluid viscosity, or a supply power condition from data stores at one or more of a monitoring device mounted on the rotating machine assembly, the remote computing device, or a database communicatively coupled to the remote computing device.

According to further examples, receiving the sensor inputs may also include receiving one or more of oil temperature information, bearing housing temperature information, oil level information, vibration information, oil water content information, oil contamination information, oil pressure information, oil flow information, or speed information associated with a shaft of the rotating machine assembly. The method may further include configuring the sensors to collect sensor data periodically, on-demand, or continuously.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems and/or devices related to monitoring several operational aspects of a bearing assembly, analyzing monitored aspects, providing predictions, alerts, and reports based on general equipment data or specific pump data.

Briefly stated, technologies are generally described for an integrated monitoring system to monitor several operational aspects of a bearing assembly, analyze monitored aspects, provide predictions, alerts, and reports based on general equipment data or specific pump data. A number of sensors in and on a bearing housing may sense a variety of operational aspects and provide input to a local or remote monitoring device. The bearing housing may include sensor mounting locations for one or more sensors. In some examples, an oil level sensor placed in a suitable mounting location on the bearing housing may detect oil levels inside the bearing housing. The monitoring device may analyze the sensor inputs in light of other information such as historic performance data, environmental information, etc. Reports, predictions, alerts, and/or suggested corrective actions may be generated based on the analysis by the monitoring device and/or remote devices communicatively coupled to the monitoring device.

Figure 1:
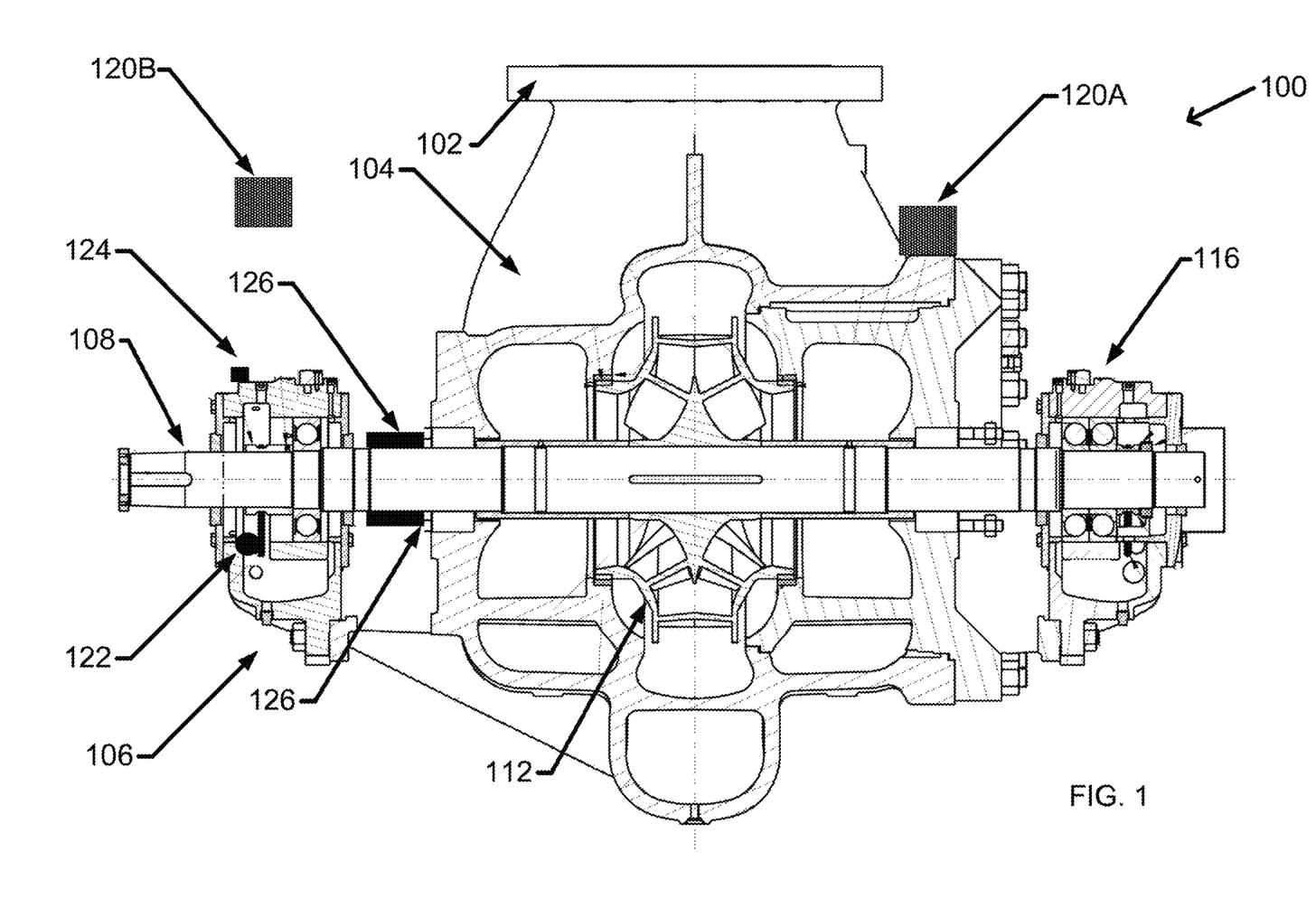
FIG. 1 illustrates an example single-stage, radially-split pump with an integrated monitoring system.

FIG. 1 illustrates an example single-stage, radially-split pump with an integrated monitoring system in accordance with at least some embodiments described herein.

As illustrated in FIG. 1, an example single-stage pump 100 may include a port 102 (intake or output), a casing 104, a first bearing housing 106, a shaft 108, an impeller 112, and second bearing housing 116. The example pump 100 may also include example sensors such as temperature sensor 122, vibration sensor 124, magnetic sensors 126, and monitoring devices 120A and/or 120B.

In an operation, fluids may enter axially through an intake port 102, and be pushed tangentially and radially outward until leaving through circumferential parts of the impeller 112 into the diffuser part of the casing 104. The fluids may gain both velocity and pressure while passing through the impeller 112. In some cases, the first bearing housing 106 may contain radial bearings and the second bearing housing 116 may include axial (thrust) bearings. In operation, the impeller 112 (and the shaft 108) is subject to different forces. While an ideal impeller would only receive rotational force from the shaft 108, axial thrust caused by unequal distribution of pressure between the front and back shrouds of an impeller (difference between the discharge pressure and suction pressure) may result in the impeller being pushed transversally to the shaft axis. The axial thrust load may result in vibration and loss of power transmission, as well as reduce expected life of pump bearings (and/or shaft). The bearings in the first bearing housing 106 and the second bearing housing 116 may, thus, be subject to detrimental forces such as thrust, vibration. Furthermore, oil or similar lubricants used inside the bearing housings may leak out or be contaminated (e.g., by shavings from the bearings). Oil temperature inside the bearing housings may also increase as a result of operational parameters (speed, acting forces, etc.), which in turn may worsen contamination or operational effectiveness of the lubricant. In yet other examples, moisture may build up inside the bearing housing further degrading an effectiveness of the lubricant.

In some examples, temperature sensors (e.g., temperature sensor 122) may be placed in or on the bearing housing to measure oil and/or frame temperature. One or more vibration sensors (e.g., vibration sensor 124) may be placed at suitable locations on the bearing housing. Other sensors that may be employed to detect operational aspects of the bearings may include an oil level sensor to detect oil level in the bearing housing, a relative humidity sensor to detect presence of water in the oil, a contamination sensor to detect contaminants in the oil, and/or a magnetic sensor to detect speed of the shaft and/or detect and store magnetic flux for diagnosis of failures, alarm conditions, and root causes. A monitoring device (120A or 120B) may be placed onto the bearing housing or be remotely located. The monitoring device may receive sensor information from the various sensors and perform analysis and take actions based on the analysis, or the monitoring device may provide raw and/or processed sensor data to a remote computing device for analysis and actions based on analysis results.

While examples are discussed using specific pumps, sensors, and communication media herein, embodiments are not limited to the example configurations. An integrated monitoring system to monitor operational aspects of a bearing assembly may be implemented in various pump types such as overhung pumps, single- or multi-stage pumps, axially split between bearing pumps, radially split barrel multi-stage pumps, vertical, double casing pumps, and similar ones. The sensors may include other types of sensors in addition to those listed herein. The components of the system may communicate through various wired or wireless communication media employing suitable communication protocols. Embodiments may also be implemented in other forms of rotating machines that utilize a shaft such as rotors, fans, etc.

Figure 2:
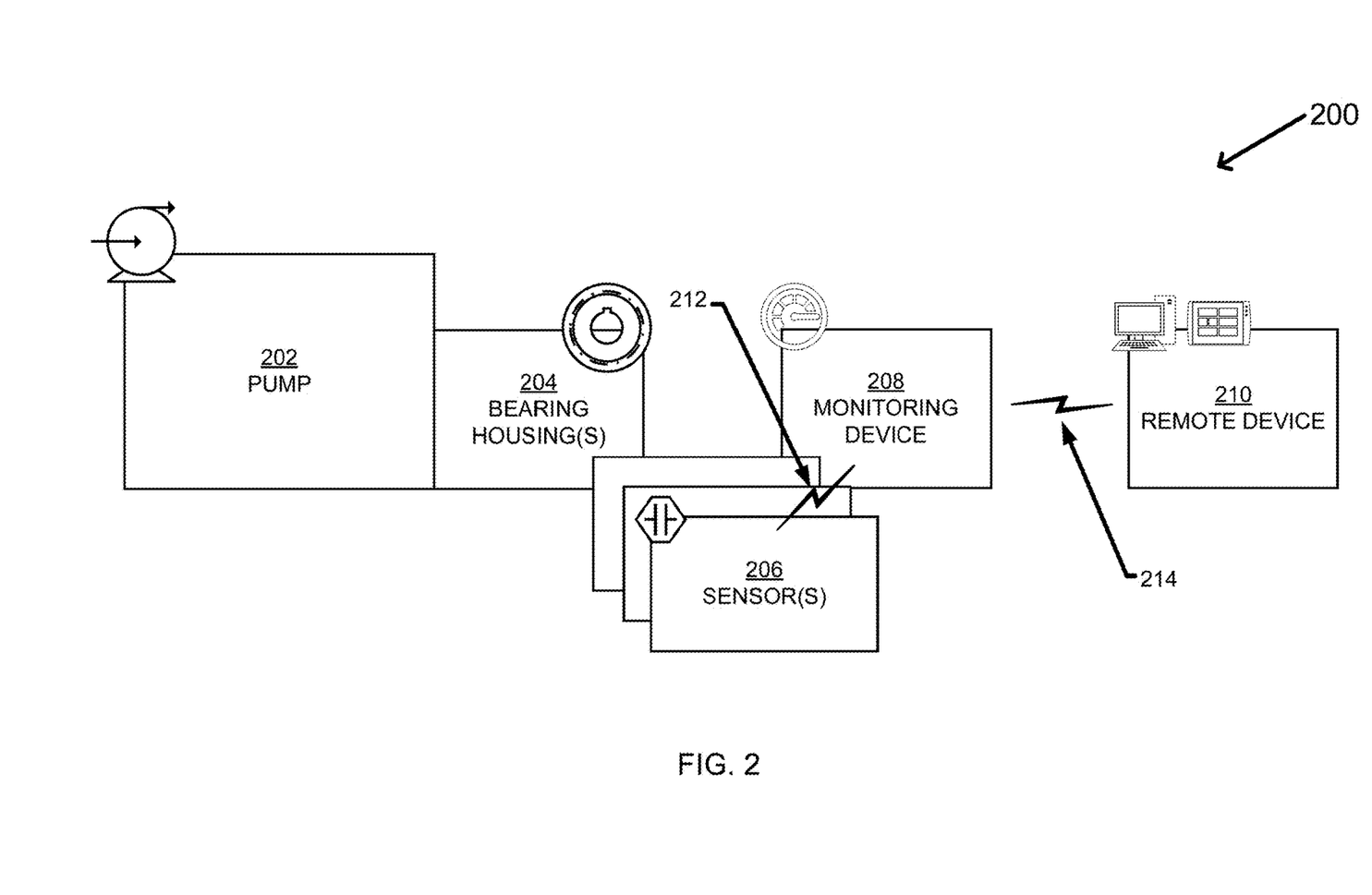
FIG. 2 is a block diagram conceptually illustrating major components of an integrated monitoring system for a centrifugal pump.

FIG. 2 is a block diagram conceptually illustrating major components of an integrated monitoring system for a centrifugal pump, arranged in accordance with at least some embodiments described herein.

System 200 in FIG. 2 includes a centrifugal pump 202, one or more bearing housings 204, a plurality of sensors 206, monitoring device 208, and remote device 210. The sensors 206 may communicate with the monitoring device 208 via communication media 212. The monitoring device 208 may communicate with the remote device 210 via communication medium (or media) 214.

Centrifugal pump 202 may be of any type described herein, but also represents other rotating machines. Bearing housing 204 is mechanically coupled to the pump 202. In some examples, multiple bearing housings may be integrated with the pump 202. Sensors 206 may be placed in or on the bearing housing(s) 204. Various sensor types and their functionality is discussed below in conjunction with FIG. 3. Sensor(s) 206 may be communicatively coupled to the monitoring device 208 through wired or wireless, electrical or optical communication media. For example, various wireless communication protocols such as near-field communication, various area networks (LAN, PAN, Bluetooth®, etc.), and similar ones may be used. The communication between the sensors and the monitoring device may be one-directional (sensor to monitoring device) or bi-directional (e.g., monitoring device may configure, reset, or otherwise control the sensors). At least some of the sensor(s) 206 may be embedded into the monitoring device 208. Remote device 210 may be a distributed control system (DCS), a desktop computer, a server, a portable computer, or a special purpose device (e.g., pump controller) communicatively coupled to the monitoring device 208 via communication media 214, which may be similar to communication media 212 or different. For example, in cases where the monitoring device is located at the pump, communication media 212 may be suitable for short-distance communication, and if the remote device 210 is located far away from the pump, communication media 214 may be suitable for longer-distance communication (e.g., WLAN, cellular communication, satellite communication, etc.). In some examples, monitoring device 208 may also be integrated with the remote device 210.

Rotating machinery such as motors, fans, rotors, and pumps include various components which may undergo wear or have equipment defects which cause failure of the components. Such components include bearings and seals which prevent leakage of the process fluid being pumped into the pump components along the shaft, for example. Any failures of the components of the rotating equipment may cause significant expense in the repair of the equipment as well as down time for the facility, where the machinery is installed. A monitoring system according to examples may detect various operational aspects of a rotating machine through sensors placed in or on a bearing housing and determine machine health based on an analysis of the detected aspects. The system may use general equipment information and/or machine specific historic data to analyze sensor information and determine actions such as alerts, reports, predictions, and/or suggest corrective actions.

An example operational aspect includes vibration. Vibration data may be collected in orthogonal directions (for example, axial and radial directions) and indicate potential problems such as unbalance, bearing defects, gear defects, blade/impeller faults, structural resonance problems, rubbing, loss of lubrication, oil whirl, cavitation/recirculation problems, machine distress and/or seal distress. For example, an increase in vibration levels may be indicative of pending failure. Based on an analysis of detected vibration levels in light of machine specific historic data, a system according to examples may predict failure within an estimated time window and issue an alert and/or suggest corrective action.

Another operational aspect includes temperature. Sensors may be used to detect temperature of the lubricant (oil), temperature of the bearing frame, and/or temperatures of various components within the bearing frame. In some examples, multiple temperature measurements may be used for a more accurate machine health analysis. For example, a modest increase in lubricant temperature may not necessarily indicate pending failure unless other components' temperatures also increase. On the other hand, an increase of temperature from multiple sensors, even if it is a few degrees may indicate a system-wide issue. Thus, a monitoring system according to examples may utilize dynamic thresholds for failure detection (as opposed to fixed temperature, vibration, etc. thresholds).

In an example configuration, the monitoring device 208 may include one or more processors and a system memory. A memory bus may be used to communicate between the processor and the system memory. Depending on the desired configuration, the processor may be of any type, including but not limited to a microprocessor (μP), a microcontroller (μC), a digital signal processor (DSP), or any combination thereof. The processor may include one or more levels of caching, such as a cache memory, a processor core, and registers. The processor core may include an arithmetic logic unit (ALU), a floating point unit (FPU), a digital signal processing core (DSP core), or any combination thereof. A memory controller may also be used with the processor, or in some implementations, the memory controller may be an internal part of the processor.

Depending on the desired configuration, the system memory may be of any type including but not limited to volatile memory (such as RAM), non-volatile memory (such as ROM, flash memory, etc.) or any combination thereof. The system memory may include an operating system, a monitoring application, and program data. The monitoring device 208 may have additional features or functionality, and additional interfaces to facilitate communications with other devices and interfaces such as external data sources and remote devices. For example, a bus/interface controller may be used to facilitate communications between the processor and one or more data storage devices via a storage interface bus. The data storage devices may be one or more removable storage devices, one or more non-removable storage devices, or a combination thereof. Examples of the removable storage and the non-removable storage devices include magnetic disk devices such as flexible disk drives and hard-disk drives (HDDs), optical disk drives such as compact disc (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer readable instructions, data structures, program modules, or other data.

The monitoring device 208 may also include an interface bus for facilitating communication from various interface devices (e.g., one or more output devices, one or more sensor interfaces, and one or more remote devices) such as a communication sub-system. Some of the example output devices may include a graphics processing unit and an audio processing unit, which may be configured to communicate to various external devices such as a display or speakers via one or more A/V ports. One or more example sensor interfaces may include a serial interface controller or a parallel interface controller, which may be configured to communicate with sensors and/or input devices (e.g., keyboard, mouse, pen, voice input device, touch input device, etc.). The communication sub-system may include a network controller, which may be arranged to facilitate communications with one or more other computing devices over a network communication link via one or more communication ports.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include non-transitory storage media.

Figure 3:
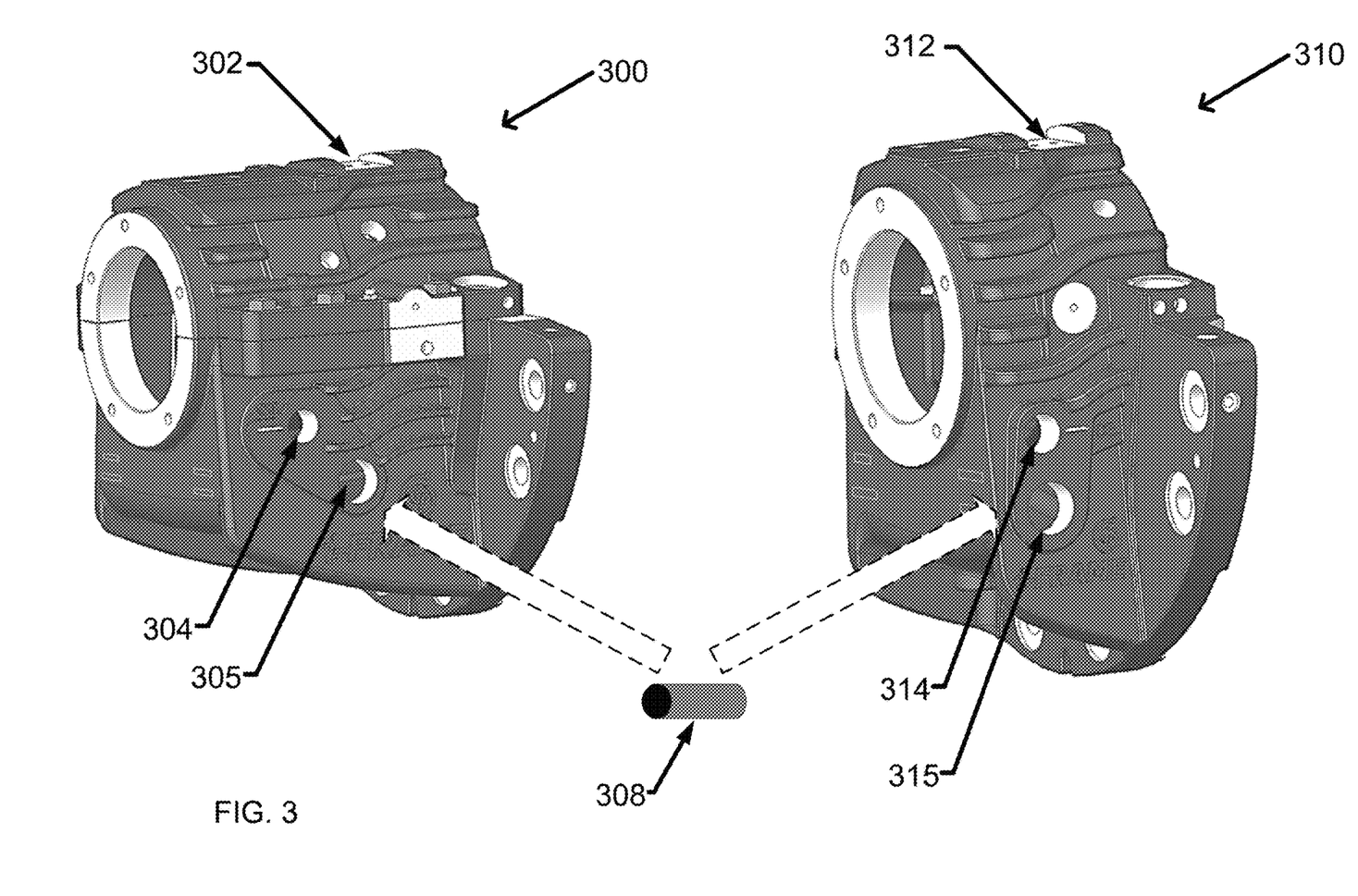
FIG. 3 illustrates two example bearing assembly frames and example locations for sensors to be placed.

FIG. 3 illustrates two example bearing assembly frames and example locations for sensors to be placed, arranged in accordance with at least some embodiments described herein.

FIG. 3 includes a first type bearing frame 300 with sensor mounting locations 302, 304, and 305, as well as, second type bearing frame 310 with sensor mounting locations 312, 314, and 315. As discussed above, centrifugal pumps have a wide spectrum of types. In each case, the bearing housing (or frame) may also be shaped and configured differently to interface with the particular type of pump. For example, first type bearing frame 300 is relatively deeper compared to the second type bearing frame 310. Thus, first type bearing frame 320 may be configured to house multiple bearings or sleeve bearings instead of ball bearings. The comparatively shallower second type bearing frame 310 may house a single bearing, for example.

In some examples, the sensors may be mounted permanently or removably inside the bearing frame, through the bearing frame, or outside the bearing frame. Location of the sensors may depend on sensor type, bearing frame type, and/or bearing frame configuration (location/size of parts inside and outside the bearing frame). An example of removable sensor placement is mounting the sensors through a threaded through-hole in the bearing frame such that sensors can be threaded in and out for replacement, for example. In other cases, sensors may be mounted on the outside of the bearing frame, for example, to detect vibration or frame temperature.

Location of the sensors may be selected based on sensor type as mentioned above. For example, frame temperature or frame vibration detection sensors may be mounted on the frame itself without a need for inside access such as locations 302 or 312 on the first and second bearing frames 300 and 310. In another example, oil level or oil contamination sensors may be placed at locations 304, 305 or 314, 315 on the first and second bearing frames 300 and 310 with access to inside locations where the oil (or lubricant) accumulates, for example, oil sump. Depending on bearing configuration and size, as well as, internal size of the bearing housing, suitable sensor mounting locations such as locations 304 and 305 may be used for the oil level sensor 308 on bearing frame 300 or locations 314, 315 on bearing frame 310. In another example, an oil level sensor may be placed in mounting location 304, which may correspond to a normal level of oil inside the bearing housing. An oil contamination sensor may be placed in mounting location 305, which may correspond to a portion of the sump that is expected to be full with oil.

The oil level sensor 308 may include capacitive interdigitated electrodes, an optical sensor, an ultrasound sensor, or an electromechanical sensor. For example, an optical sensor may transmit a visible light into the bearing housing and detect reflected light to distinguish the level of oil inside. An ultrasound sensor may utilize transmitted and reflected sound waves to detect oil level inside the bearing housing. In yet other examples, the oil level sensor may be an electromechanical sensor such as a floating switch sensor.

Figure 4:
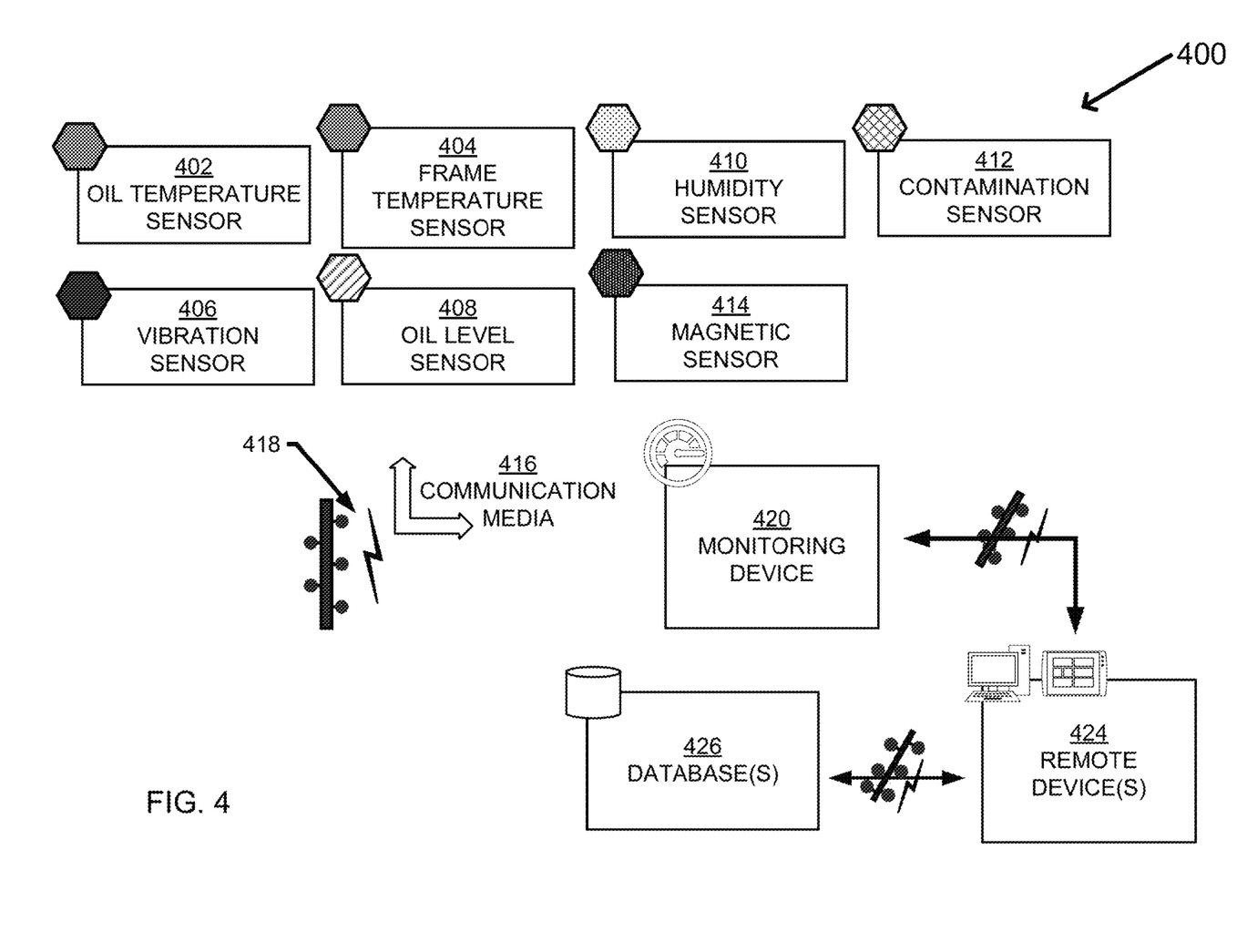
FIG. 4 is a conceptual illustration of various example sensors and interactions between components of a monitoring system.

FIG. 4 is a conceptual illustration of various example sensors and interactions between components of a monitoring system, arranged in accordance with at least some embodiments described herein.

Example system 400 includes oil temperature sensor 402, frame temperature sensor 404, vibration sensor 406, oil level sensor 408, relative humidity sensor 410, contamination sensor 412, and magnetic sensor 414. The example system also includes monitoring device 420 communicatively coupled to the sensors via communication media 416, which may include wired and/or wireless means 418, one or more remote device(s) 424 and one or more databases 426.

Monitoring device 420 and remote device(s) 424 may function and communicate with each other (and the sensors) similar to the monitoring device 208 and remote device 210 discussed in conjunction with FIG. 2. Database(s) 426 may store generic equipment information such as pump specifications; machine-specific information such as each particular pump's failure history, performance history, load history, etc.; and/or environmental information such as ambient temperature, ambient vibration levels, pumped fluid pressure, pumped fluid temperature, pumped fluid viscosity, or a supply power condition (e.g., voltage level changes, power line noise), etc. In some examples, some of the aforementioned information such as generic equipment information may be stored at the monitoring device 420 and/or remote device(s) 424.

Oil temperature sensor 402 may sense a temperature of the bearing lubricant during operation. An increase in the temperature may indicate abnormal operation. However, in some cases, the temperature may increase due to environmental changes (e.g., increase in environment temperature) or a change in the pumped fluid (e.g., viscosity of the pumped fluid increasing). Thus, the sensed temperature may be evaluated in light of other factors such as those discussed above. Frame temperature sensor 404 may sense a temperature of the bearing frame (housing). In a relatively larger pump system, certain locations of the bearing housing may heat before the oil temperature increases or vice versa. Thus, sensing frame temperature at one or more locations in addition to oil temperature may provide valuable input to a system analyzing pump health.

Vibration sensor 406 may detect vibration levels at one or more locations of the bearing housing. As discussed above, vibration may be indicative of a number of pending failure or potential problems. In some cases, the volume of lubricant inside the bearing housing may decrease over time due to leakage or other reasons. Oil level sensor 408 placed at a suitable location to detect changes in lubricant level may allow detection of oil level decrease before it reaches a critical threshold. The oil level sensor 408 may be capacitive interdigitated electrodes among other types. Relative humidity sensor 410 may detect presence and/or concentration of water in the lubricant in % RH and help predict pending problems due to water in the lubricant. Trend data associated with water content in the lubricant may also be captured to diagnose 'rapid' changes in % RH (PPM) over a period of time. Contamination sensor 412 may detect solid or liquid contaminants in the lubricant other than water. Contaminants may accumulate between the bearings and affect bearing operations, accumulate in oil channels and prevent lubricant flow, etc. Contaminant sensor 412 may detect contaminants optically, through ultrasound detection, or other mechanisms. Magnetic sensor 414 may be used to detect a rotating speed of the shaft through the use of magnets or other ferrous materials embedded into drive/driven shaft or any other rotating element within the rotating equipment. Magnetic sensor 414 may also be used to detect and measure magnetic flux. Magnetic flux data may be captured and stored for analysis (e.g., through AI) to diagnose potential motor failures, alarm conditions, and root causes.

Sensors that may be used in conjunction with a monitoring system according to examples are not limited to the illustrative examples discussed herein. Other types of sensors, for example, flow sensors or pressure sensors may be used to monitor other operational aspects of the pump or rotating machine. In some examples, different sensors may be integrated. Some of the sensors may be placed permanently inside or on the bearing housing. Other sensors may be removable so that they can be replaced during a lifetime of the pump or rotating machine. The sensors may be configured to collect data periodically, on-demand, or continuously. In some cases, sensor data may be used for dynamic analysis, that is, decisions on pending failure or other equipment problems may not be made based on a fixed threshold of a single sensor. For example, sensed oil temperature may be evaluated in light of other sensor inputs such as frame temperature, oil contamination, etc.

Figure 5:
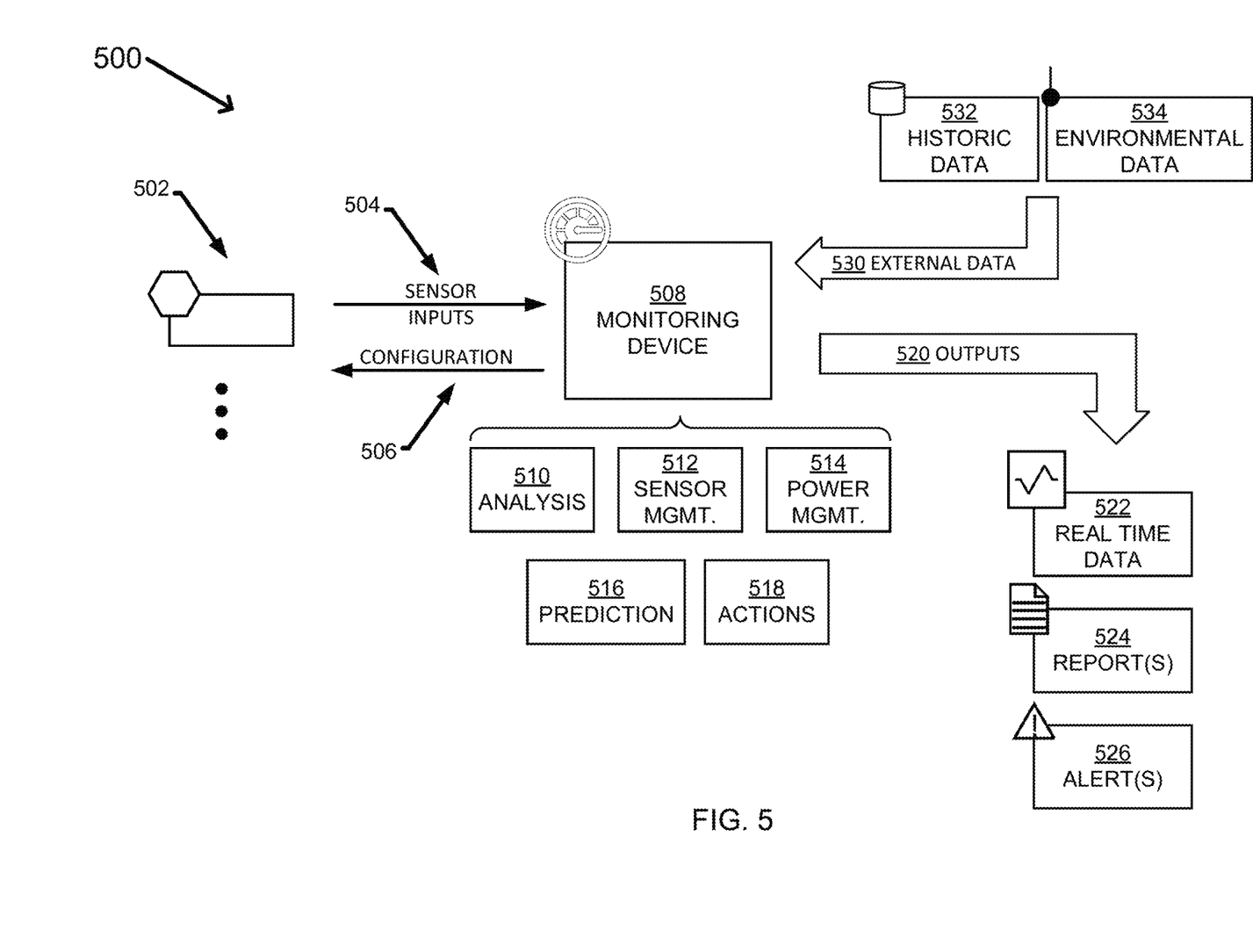
FIG. 5 conceptually illustrates operations, inputs, and outputs of an example monitoring system.

FIG. 5 conceptually illustrates operations, inputs, and outputs of an example monitoring system, arranged in accordance with at least some embodiments described herein.

Diagram 500 includes monitoring device 508 receiving sensor inputs 504 from sensors 502 and providing configuration information 506 to the sensors 502. Monitoring device 508 may be responsible for analysis 510 of received sensor data, sensor operation management 512, power management 514, prediction of equipment failure 516, and suggestion of corrective actions 518. Outputs 520 of the monitoring device 508 may include real time data 522, reports 524, and alerts 526. Monitoring device 508 may also receive external data 530 such as historic data 532 and environmental data 534.

Analysis 510 may include evaluation of sensor inputs 504 in light of historic data 532 and environmental data 534. The historic data 532 may include general equipment specifications or machine specific historic performance/failure information. The analysis may employ dynamic thresholds based on multiple sensor inputs. Machine learning algorithms and/or artificial intelligence algorithms may be employed for the analysis. In addition to the analysis 510, monitoring device 508 may manage the sensors 502 by transmitting reset, configuration, or other instructions to the sensors. Monitoring device 508 may also manage power to itself and/or sensors. The power may be supplied by an external power source or a renewable power supply. For example, a power supply may generate power from the rotation of the shaft, from solar power, or battery power to supply the monitoring device and/or the sensors.

Monitoring device 508 may be configured to predict equipment performance such as pending failure or needed part replacements based on the analysis 510. The prediction 516 may be used to suggest corrective actions 518 such as replacement of lubricant, particular components, change of operational parameters, etc. Monitoring device 508 may provide raw or processed real time data 522 from the sensors to external devices such as servers, stationary or portable computing devices, special purpose computing devices, output devices (e.g., printers, displays), etc. Monitoring device 508 may also provide reports 524 based on the analysis 510 and/or alerts 526. In some examples, one or more of the operations performed by the monitoring device 508 may be performed in parallel or in place of the monitoring device by one or more external devices. Thus, the monitoring device 508 may vary between a "smart" module performing all or most of the operations and a "dumb" module that collects and forward collected sensor data to an external device for processing.

Figure 6:
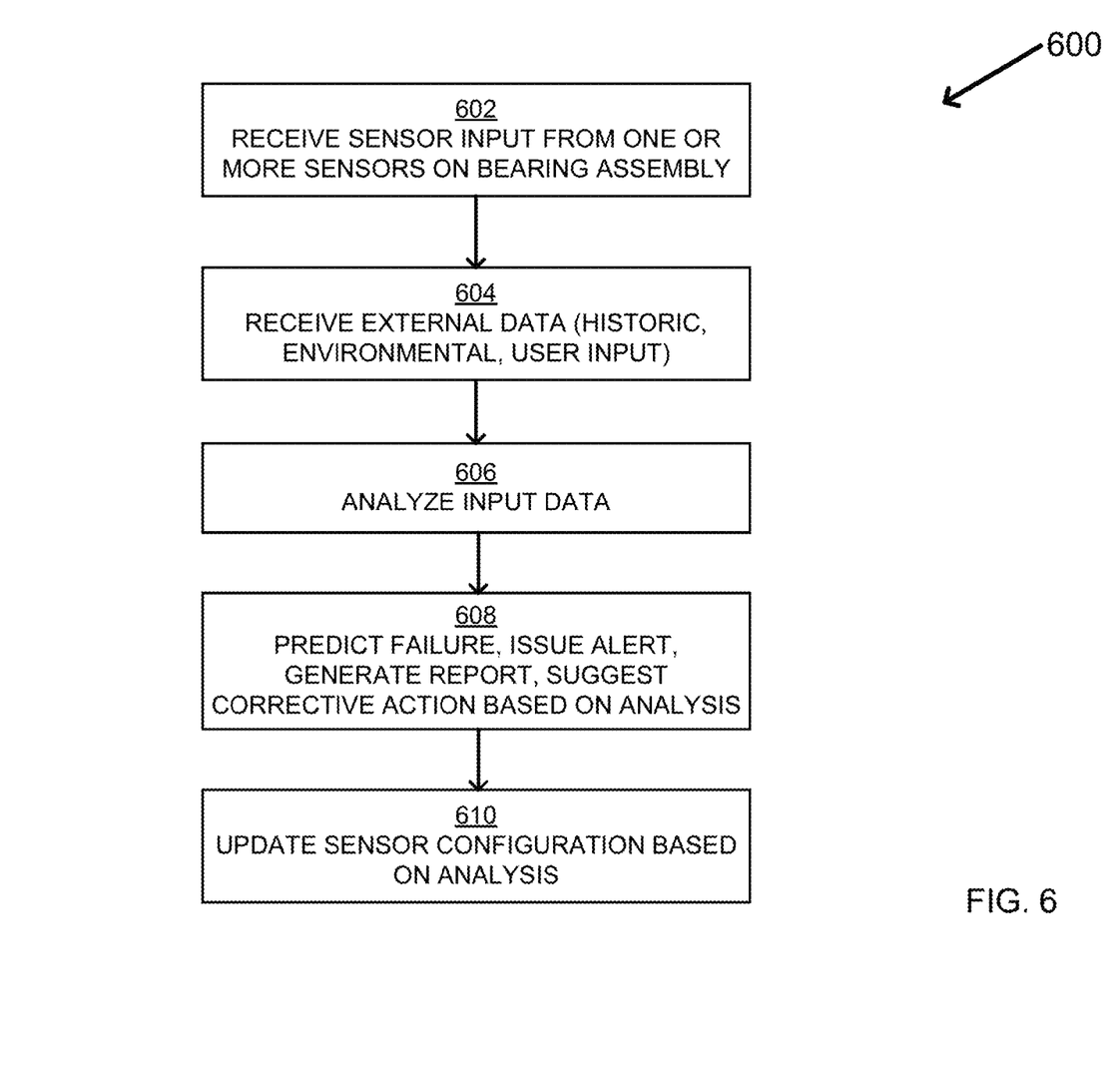
FIG. 6 is a flow diagram illustrating operations of an example monitoring system, arranged in accordance with at least some embodiments described herein.

FIG. 6 is a flow diagram illustrating operations of an example monitoring system, arranged in accordance with at least some embodiments described herein.

Example methods may include one or more operations, functions or actions as illustrated by one or more of blocks 602, 604, 606, 608, and 610, and may in some embodiments be performed by a computing device or may be performed by an apparatus controlling operations of a system such as the one described in FIG. 2. The operations described in the blocks 602-610 may also be stored as computer-executable instructions in a computer-readable medium of a computing device.

An example process to monitor operational aspects of a centrifugal pump (or similar rotating machine) may begin with block 602, "RECEIVE SENSOR INPUT FROM ONE OR MORE SENSORS ON BEARING ASSEMBLY," where electrical or optical signals carrying information associated with sensed operational aspects of a centrifugal pump or similar rotating machine. The sensors providing the information may include, but are not limited to, an oil temperature sensor, a frame temperature sensor, a vibration sensor, an oil level sensor, a relative humidity sensor, a contamination sensor, and a magnetic sensor.

Block 602 may be followed by block 604, "RECEIVE EXTERNAL DATA (HISTORIC, ENVIRONMENTAL, USER INPUT)," where a computing device such as monitoring device 420 or remote device 424 in FIG. 4 may receive external data such as historic operational data for the specific pump or generic operational data for the family of pumps, environmental data for a location of the pump, and/or user input (e.g., configuration information).

Block 604 may be followed by block 606, "ANALYZE INPUT DATA," where received sensor information may be analyzed in light of the received external data.

Block 606 may be followed by block 608, "PREDICT FAILURE, ISSUE ALERT, GENERATE REPORT, SUGGEST CORRECTIVE ACTION BASED ON ANALYSIS," where based on the analysis, a failure prediction, an alert, a performance report, or a suggested corrective action may be issued.

Block 608 may be followed by block 610, "UPDATE SENSOR CONFIGURATION BASED ON ANALYSIS," where sensor configuration (e.g., frequency of sensing, sensitivity level of particular sensors, etc.) may be modified or updated based on the analysis results.

The operations included in the process described above are for illustration purposes and may be implemented by similar processes with fewer or additional operations, as well as in different order of operations using the principles described herein. The operations described herein may be executed by one or more processors operated on one or more computing devices, one or more processor cores, and/or specialized processing devices, among other examples.

Disclosed herein are methods and devices to monitor operational aspects of pumps or similar rotating machines. The benefits of the presently disclosed monitoring system are numerous. For example, health of a rotating machine may be monitored in real time and reports, alerts, predictions about potential failures may be generated based on analysis of the monitored aspects. Thus, equipment failures may be detected/predicted before the rotating machine stops or worse, a catastrophic failure occurs. In some cases, components may be replaced based on monitoring results avoiding waste of resources for early replacement or equipment downtime due to actual failure, which may be expected in schedule-based maintenance. Furthermore, accuracy of reports or predictions may be increased by using machine specific historic information in combination with the sensor inputs. In some examples, an integrated system may also provide suggested corrective actions based on the analysis, avoiding a need to contact manufacturer or service entities for each detected anomaly. The monitoring system may be integrated into service and maintenance programs. By continuously monitoring system health and planning actions when necessary, costly unscheduled downtimes and repairs may be avoided.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only and is not intended to be limiting.

The herein described subject matter sometimes illustrates different components contained within, or connected with, different other components. Such depicted architectures are merely examples, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A monitoring system for a rotating machine, the monitoring system comprising:
   a first sensor and a second sensor mounted in a bearing housing of the rotating machine, wherein the first sensor is an oil level sensor mounted at a location in the bearing housing suitable to detect a lubricant oil level inside the bearing housing and the second sensor is distinct from the first sensor; and
   a monitoring device communicatively coupled to the first sensor and second sensor, the monitoring device comprising:
      a communication sub-system to facilitate communication with the first sensor and second sensor;
      a memory configured to store instructions; and
      a processor coupled to the communication sub-system and the memory, the processor, in conjunction with the instructions stored in the memory, configured to:
         receive sensor inputs from the first sensor and second sensor;
         perform an analysis of the received sensor inputs to render a decision on a pending failure or an equipment problem, wherein the analysis includes evaluation of each sensor input in light of one or more other sensor inputs and excludes application of a fixed threshold to a single sensor input to render the decision; and
         generate an alert based on the rendered decision as a result of the analysis.

2. The monitoring system of claim 1, wherein
the communication sub-system is further configured to facilitate one or more of wired and wireless communication with one or more remote devices, and
the processor is further configured to:
transmit the generated alert to the one or more remote devices, wherein the alert includes one or more of a prediction, a report, or a suggested corrective action; and
transmit raw or processed sensor inputs to the one or more remote devices such that at least a portion of the analysis is performed by the one or more remote devices, wherein the one or more remote devices comprise a distributed control system (DCS), a server, a stationary computing device, a portable computing device, a special purpose computing device, or an output device.

3. The monitoring system of claim 1, wherein the processor is further configured to:
receive one or more of historical data or environmental data, wherein the historical data includes one or more of generic rotating machine specifications, specific rotating machine specifications, historic performance data for the rotating machine, or historic failure data for the rotating machine, and the environmental data includes one or more of ambient temperature, ambient vibration levels, fluid pressure, fluid temperature, fluid viscosity, or a supply power condition; and
perform the analysis of the received sensor inputs in conjunction with the received one or more of historical data or environmental data.

4. The monitoring system of claim 1, wherein the processor is further configured to transmit one or more of reset or configuration instructions to the first sensor and second sensor.

5. The monitoring system of claim 1, wherein the second sensor includes:
an oil temperature sensor configured to measure a temperature of the lubricant oil,
a bearing housing temperature sensor configured to measure a temperature of the bearing housing,
a vibration sensor configured to collect vibration data in at least two orthogonal directions,
a relative humidity sensor configured to sense one or more of a presence of water or a concentration of water in a lubricant of the bearing housing,
an oil contamination sensor configured to sense one or more of a presence of a contaminant or a concentration of the contaminant in the lubricant oil,
a magnetic sensor configured to sense a rotational speed of a shaft of the rotating machine,
a pressure sensor configured to measure a pressure of the lubricant oil, or
a flow sensor configured to measure a flow rate of the lubricant oil through a filtering system.

6. The monitoring system of claim 1, wherein
each of the first sensor and second sensor are mounted inside or on the surface of the bearing housing permanently or removably, and
a location of each sensor is selected based on one or more of a sensor type, a bearing housing type, or a bearing housing configuration.

7. The monitoring system of claim 1, wherein the location in the bearing housing suitable to mount the oil level sensor is selected based on one or more of a size of a bearing, a configuration of the bearing, an inside volume of the bearing housing, or a type of the lubricant oil.

8. The monitoring system of claim 1, wherein the first sensor and second sensor are configured to collect sensor data periodically, on-demand, or continuously.

9. A monitoring system for a rotating machine, the monitoring system comprising:
a first sensor and a second sensor mounted in a bearing housing of the rotating machine, wherein the first sensor is an oil level sensor mounted at a location in the bearing housing suitable to detect a lubricant oil level inside the bearing housing and the second sensor is distinct from the first sensor;
a remote computing device; and
a monitoring device communicatively coupled to the first sensor and second sensor and the remote computing device, the monitoring device comprising:
a communication sub-system to facilitate communication with the first sensor and second sensor and the remote computing device;
a memory configured to store instructions; and
a processor coupled to the communication sub-system and the memory, the processor, in conjunction with the instructions stored in the memory, configured to:
receive sensor inputs from the first sensor and second sensor;
transmit at least a first portion of the received sensor inputs to the remote computing device;
perform an analysis on a second portion of the received sensor inputs to render a decision on a pending failure or an equipment problem, wherein the analysis includes evaluation of each sensor input of the second portion in light of one or more other sensor inputs and excludes application of a fixed threshold to a single sensor input to render the decision; and
generate an alert based on the rendered decision as a result of the analysis.

10. The monitoring system of claim 9, wherein the remote computing device is configured to:
receive one or more of historical data or environmental data, wherein the historical data includes one or more of generic rotating machine specifications, specific rotating machine specifications, historic performance data for the rotating machine, or historic failure data for the rotating machine, and the environmental data includes one or more of ambient temperature, ambient vibration levels, fluid pressure, fluid temperature, fluid viscosity, or a supply power condition;
perform an analysis on the first portion of the received sensor inputs in conjunction with the received one or more of historical data or environmental data, wherein the analysis includes evaluation of each sensor input of the first portion in light of one or more other sensor inputs and excludes application of a fixed threshold to a single sensor input to render the decision; and
generate a report based on a result of the analysis.

11. The monitoring system of claim 9, wherein one or more of the historical data and the environmental data is stored at least partially in one or more of the monitoring device, the remote computing device, or a database communicatively coupled to the remote computing device.

12. The monitoring system of claim 9, wherein the monitoring device is mounted on the bearing housing or integrated with the remote computing device.

13. The monitoring system of claim 12, wherein the processor is configured to employ one or more of a machine learning algorithm or an artificial intelligence algorithm to perform the analysis and to generate one or more of a prediction, the alert, a report, or a suggested corrective action.

14. The monitoring system of claim 9, wherein the oil level monitoring device includes capacitive interdigitated electrodes, an optical sensor, an ultrasound sensor, or an electromechanical sensor.

15. The monitoring system of claim 9, wherein the first sensor includes an oil temperature sensor, a bearing housing temperature sensor, a vibration sensor, a relative humidity sensor, an oil contamination sensor, a pressure sensor, a flow sensor, or a magnetic sensor.

16. A method to monitor operational health of a rotating machine assembly, the method comprising:
   receiving sensor inputs from a first sensor and a second sensor mounted in a bearing housing of the rotating machine assembly, wherein the first sensor is an oil level sensor mounted at a location in the bearing housing suitable to detect a lubricant oil level inside the bearing housing and the second sensor is distinct from the first sensor;
   transmitting at least a first portion of the received sensor inputs to a remote computing device;
   receiving external data associated with the rotating machine assembly;
   performing an analysis on a second portion of the received sensor inputs in conjunction with the received external data to render a decision on a pending failure or an equipment problem by evaluating each sensor input of the second portion in light of one or more other sensor inputs and excluding application of a fixed threshold to a single sensor input to render the decision; and
   generating an alert that includes a suggested corrective action based on the rendered decision as a result of the analysis.

17. The method of claim 16, wherein transmitting at least the first portion of the received sensor inputs to the remote computing device comprises:
   facilitating performance of an analysis, by the remote computing device, on the first portion of the received sensor inputs in conjunction with the received external data by applying a dynamic threshold in evaluation of each sensor input of the first portion based on one or more other sensor inputs; and
   facilitating generation of another alert, by the remote computing device, based on a result of the analysis.

18. The method of claim 16, wherein receiving the external data comprises:
   receiving one or more of generic rotating machine specifications, specific rotating machine specifications, historic performance data for the rotating machine, or historic failure data for the rotating machine, and one or more of ambient temperature, ambient vibration levels, fluid pressure, fluid temperature, fluid viscosity, or a supply power condition from data stores at one or more of a monitoring device mounted on the rotating machine assembly, the remote computing device, or a database communicatively coupled to the remote computing device.

19. The method of claim 16, wherein receiving the sensor inputs comprises:
   receiving one or more of oil temperature information, bearing housing temperature information, oil level information, vibration information, oil water content information, oil contamination information, oil pressure information, oil flow information, or speed information associated with a shaft of the rotating machine assembly.

20. The method of claim 16, further comprising:
   configuring the sensors to collect sensor data periodically, on-demand, or continuously.

* * * * *